(12) United States Patent
Sprengard-Eichel et al.

(10) Patent No.: US 6,791,004 B2
(45) Date of Patent: Sep. 14, 2004

(54) ABSORBENT ARTICLE WITH THERMAL CELL ACTUATOR

(75) Inventors: Cornelia Sprengard-Eichel, Frankfurt (DE); Mark James Kline, Okeana, OH (US); Bruno Johannes Ehrnsperger, Bad Soden am Taunus (DE); Tracey Elaine Beckman, Milford, OH (US); Constance Lee Fisher, Springdale, OH (US); Mattias Schmidt, Idstein (DE); Donald Carroll Roe, West Chester, OH (US); Bruce Ernest Tepper, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 106 days.

(21) Appl. No.: 09/778,371

(22) Filed: Feb. 7, 2001

(65) Prior Publication Data

US 2001/0023340 A1 Sep. 20, 2001

Related U.S. Application Data

(63) Continuation-in-part of application No. 09/504,765, filed on Feb. 15, 2000, now Pat. No. 6,572,600, and a continuation-in-part of application No. 09/504,485, filed on Feb. 15, 2000, now Pat. No. 6,565,549.

(51) Int. Cl.[7] ............................ A61F 13/15; A61F 13/20
(52) U.S. Cl. ...................... 604/361; 604/362; 604/364
(58) Field of Search ................................ 604/361, 362, 604/364, 359, 385.01

(56) References Cited

U.S. PATENT DOCUMENTS

| | | | |
|---|---|---|---|
| 3,175,558 A | | 3/1965 | Caillouette et al. |
| 3,643,665 A | | 2/1972 | Caillouette |
| 3,871,376 A | * | 3/1975 | Kozak .................. 604/291 |
| 3,951,127 A | | 4/1976 | Watson et al. |
| 4,077,390 A | | 3/1978 | Stanley et al. |
| 4,303,571 A | | 12/1981 | Jansen et al. |
| 4,386,932 A | * | 6/1983 | Pitts ...................... 604/383 |
| 4,451,383 A | | 5/1984 | Arrhenius |
| 4,460,546 A | | 7/1984 | Kapralis et al. |
| 4,462,224 A | | 7/1984 | Dunshee et al. |
| 4,470,263 A | * | 9/1984 | Lehovec et al. ............ 62/3.5 |
| 4,483,021 A | * | 11/1984 | McCall ...................... 2/7 |
| 4,515,595 A | | 5/1985 | Kievit et al. |

(List continued on next page.)

FOREIGN PATENT DOCUMENTS

| | | | | |
|---|---|---|---|---|
| WO | WO 96/19168 | | 6/1996 | |
| WO | WO 98/29079 | | 7/1998 | |
| WO | WO 99/45973 | | 9/1999 | |
| WO | WO 0066051 | * | 9/2000 | ......... A61F/7/00 |

*Primary Examiner*—John J. Calvert
*Assistant Examiner*—Michele Kidwell
(74) *Attorney, Agent, or Firm*—David M. Weirich; Edward J. Milbrada; Caroline Wei-Berk

(57) ABSTRACT

An absorbent article which includes a thermal cell actuator capable of adding or removing heat to or from at least a portion of the absorbent article to perform a useful function on the article. The thermal cell actuator may be activated by an action of the wearer or caregiver or by environmental conditions between the article and wearer.

15 Claims, 4 Drawing Sheets

U.S. PATENT DOCUMENTS

| | | | | |
|---|---|---|---|---|
| 4,543,154 | A | 9/1985 | Reiter | |
| 4,572,864 | A | 2/1986 | Benson et al. | |
| 4,580,547 | A | 4/1986 | Kapralis et al. | |
| 4,596,250 | A * | 6/1986 | Beisang et al. | 607/114 |
| 4,665,308 | A | 5/1987 | Courvoisier et al. | |
| 4,705,935 | A | 11/1987 | Traffanstedt et al. | |
| 4,741,338 | A | 5/1988 | Miyamae | |
| 4,851,291 | A | 7/1989 | Vigo et al. | |
| 4,860,748 | A | 8/1989 | Chiurco et al. | |
| 4,891,501 | A | 1/1990 | Lipton | |
| 4,899,772 | A | 2/1990 | Rao | |
| 4,920,964 | A | 5/1990 | Francis, Jr. | |
| 4,962,761 | A * | 10/1990 | Golden | 128/400 |
| 4,967,573 | A | 11/1990 | Wilhelm | |
| 5,056,589 | A | 10/1991 | Hettel et al. | |
| 5,143,048 | A | 9/1992 | Cheney, III | |
| 5,167,655 | A * | 12/1992 | McCoy | 604/396 |
| 5,197,294 | A | 3/1993 | Galvan et al. | |
| 5,230,333 | A | 7/1993 | Yates et al. | |
| 5,275,156 | A | 1/1994 | Milligan et al. | |
| 5,366,801 | A | 11/1994 | Bryant et al. | |
| 5,417,276 | A | 5/1995 | Dobry | |
| 5,423,996 | A | 6/1995 | Salyer | |
| 5,431,022 | A | 7/1995 | Abe | |
| 5,431,622 | A * | 7/1995 | Pyrozyk et al. | 602/2 |
| 5,476,490 | A | 12/1995 | Silver | |
| 5,486,680 | A | 1/1996 | Lieberman | |
| 5,520,274 | A | 5/1996 | Huber | |
| 5,534,020 | A * | 7/1996 | Cheney et al. | 607/108 |
| 5,545,197 | A | 8/1996 | Bowen | |
| 5,552,075 | A | 9/1996 | Salyer | |
| 5,649,914 | A | 7/1997 | Glaug et al. | |
| 5,650,090 | A | 7/1997 | Salyer | |
| 5,662,096 | A | 9/1997 | Walters | |
| 5,702,375 | A * | 12/1997 | Angelillo et al. | 604/358 |
| 5,722,482 | A | 3/1998 | Buckley | |
| 5,736,110 | A | 4/1998 | Angelillo et al. | |
| 5,741,318 | A | 4/1998 | Ouellette et al. | |
| 5,769,832 | A * | 6/1998 | Hasse | 604/359 |
| 5,772,185 | A | 6/1998 | Pulsipher | |
| 5,792,213 | A | 8/1998 | Bowen | |
| 5,797,892 | A | 8/1998 | Glaug et al. | |
| 5,800,490 | A * | 9/1998 | Patz et al. | 607/108 |
| 5,805,766 | A | 9/1998 | Wang | |
| 5,865,823 | A * | 2/1999 | Curro | 604/367 |
| 5,885,475 | A | 3/1999 | Salyer | |
| 5,897,580 | A | 4/1999 | Silver | |
| 5,918,590 | A | 7/1999 | Burkett et al. | |
| 5,984,995 | A * | 11/1999 | White | 75/230 |
| 6,102,936 | A * | 8/2000 | Augustine et al. | 607/96 |
| 6,153,209 | A * | 11/2000 | Vega et al. | 424/404 |
| 6,308,341 | B1 * | 10/2001 | Shelton | 2/400 |
| 6,320,095 | B1 * | 11/2001 | Wall | 604/368 |
| 6,399,853 | B1 * | 6/2002 | Roe et al. | 604/362 |
| 6,407,308 | B1 * | 6/2002 | Roe et al. | 604/361 |
| 6,440,156 | B1 * | 8/2002 | Augustine et al. | 607/96 |

* cited by examiner

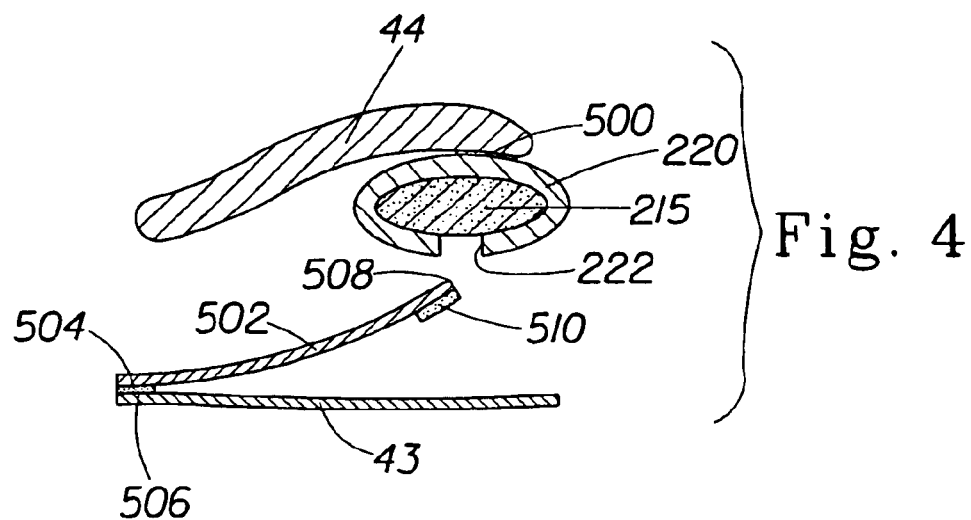
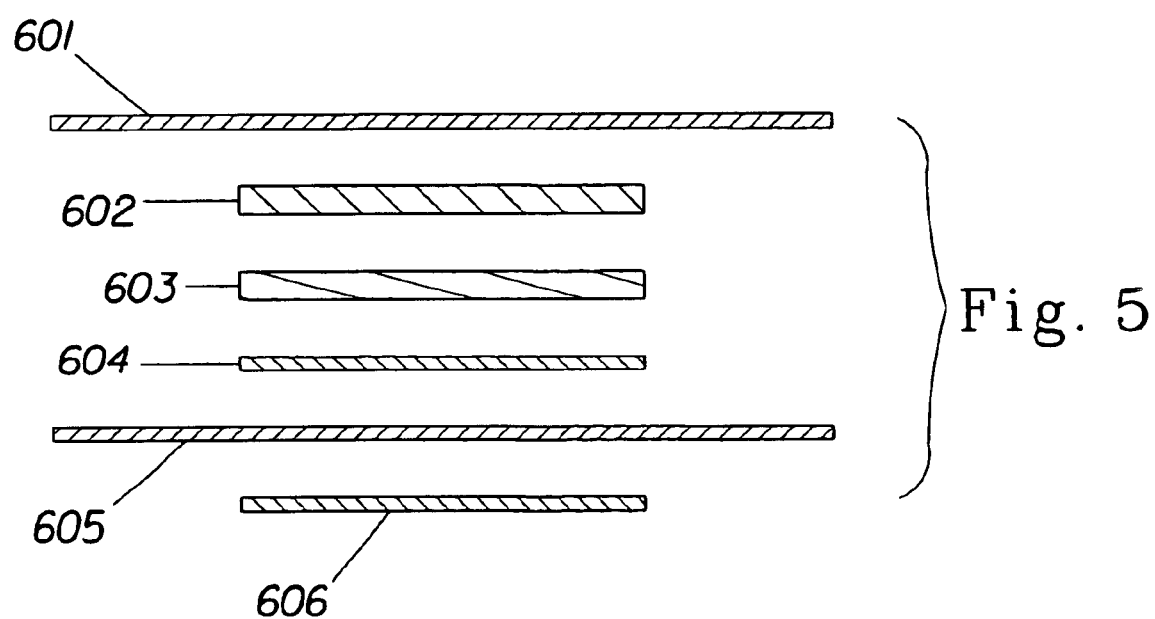

ABSORBENT ARTICLE WITH THERMAL CELL ACTUATOR

CROSS REFERENCE TO RELATED APPLICATIONS

This patent application is a continuation-in-part of application Ser. No. 09/504,765, filed Feb. 15, 2000, now U.S. Pat. No. 6,572,600 in the names of Roe et al., and a continuation-in-part of application Ser. No. 09/504,485, filed Feb. 15, 2000, now U.S. Pat. No. 6,565,549 in the names of Allen et al.

FIELD OF THE INVENTION

This invention is directed to hygienic absorbent articles, such as diapers, adult incontinence articles, feminine protection articles and the like. More particularly, the invention relates to absorbent articles including a thermal cell actuator.

BACKGROUND OF THE INVENTION

Absorbent articles are well known in the art. These articles typically have an absorbent core, which is held or positioned against the body of the wearer during use by a fastening system, such that bodily exudates are caught by the article. Typical absorbent articles include a topsheet facing the wearer which permits fluid exudates to pass through and a backsheet which prevents the exudates from escaping from the absorbent article.

Many advancements have been made in the art since the introduction of the disposable absorbent article. However, problems still exist relating to ease of application of the article to the wearer and isolation of bodily waste. Attempts have been made to isolate fecal waste by employing pockets, topsheets with receiving apertures, spacing elements, barrier cuffs, and other physical means. In some cases, such structures have the deficiency of inadequately maintaining coordination with the wearer's body, especially the waste outlet points and/or the portions of the wearer's body near the perimeter of the product. Attempts have also been made to improve the application of the article to the wearer by the use of adhesive tapes and mechanical fastening systems such as Velcro®. However, the articles are still difficult to apply to mobile wearers using only two hands.

In an effort to overcome the deficiencies of the prior art, topical adhesives such as hydrocolloid, silicone, and hydrogel adhesives have been incorporated into disposable articles as a means of better positioning the article or maintaining body contact. However, the addition of such adhesives can have the negative effects of complication of removal of the product because they adhere aggressively to the wearer's skin and/or other components of the disposable article. However, without supplemental sources of heating or cooling to activate or deactivate the thermally activatable or thermally deactivateable adhesive, the specific adhesive choice may be practically limited, for example to adhesives which are activatable at or near body temperature and deactivatable below or near body temperature.

In U.S. Pat. Nos. 5,649,914 and 5,797,892; a toilet training aid is disclosed which generates a heating or cooling effect in the presence of urine from the wearer within the article. The heating or cooling effect is intended to cause the wearer discomfort in an attempt to aid in the toilet training process. This heating or cooling effect performs no useful function upon the article itself. Instead, the toilet training aid acts upon the wearer to cause the wearer to take some action (i.e., remove the wet article and apply a new one). Further, the toilet training aid responds solely to conditions within the article itself, not to conditions between the article and the wearer. Further, the toilet training aid is only functioning for a short period of time and is not designed to provide a sustained reduction in relative humidity or temperature for typical wear times.

Also, absorbent articles tend to have elements which have the same or essentially the same properties upon application as during the wearing period. For example, while the tension in stretch panels changes once a stretch diaper is applied to a wearer, the modulus of the materials comprising the stretch panels remains essentially constant other than minor hysteresis loss. The lack of change in properties of materials or structures between application and wearing of the article can result in failure to optimize both the properties during application of the article and the properties during wearing. Compromises may result which minimize the overall effectiveness of the article or make application of the article more difficult. While heat shrinkable materials have been used in the process of constructing absorbent articles, such as to contract a portion such as a waistband thus changing its properties, such articles do not react to or change properties given a temperature change following the manufacturing process. Post-manufacturing changes in material properties may be attained by using heating or cooling element as disclosed in the present invention.

Therefore, it would be desirable to provide a thermal cell actuator which performs a useful function on an absorbent article, such as changing properties of at least a portion of the article or the altering the conditions between the article and the wearer. That is, it would be desirable for absorbent articles to include a "thermal cell actuator" which actuates some useful function.

SUMMARY OF THE INVENTION

The present invention solves the deficiencies of the prior art by providing an absorbent article comprising: a topsheet, a backsheet joined with at least a portion of the topsheet, an absorbent core disposed between at least a portion of the topsheet and the backsheet; and a thermal cell actuator capable of adding or removing heat to or from at least a portion of the absorbent article to perform a useful function on the article. The thermal cell actuator can be activated by the wearer, caregiver, or environment conditions between the article and the wearer at the point in time the heat addition or removal is needed.

BRIEF DESCRIPTION OF THE DRAWINGS

FIG. 4 are isometric and cross sectional views of a tensile force to peel a tab exposing an opening in the thermal cell actuator.

FIG. 5 is cross sectional view indicating potential placement locations of the present invention.

DETAILED DESCRIPTION OF THE INVENTION

As used herein, the term "absorbent article" refers to devices which absorb and/or contain body exudates and, more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as absorbent articles (i.e., they are intended to be discarded after a single use and, preferably, to be recycled, composted or otherwise discarded in an environmentally compatible manner). A "unitary" absorbent article refers to absorbent articles which are formed of separate parts united together to form a coordinated entity so that they do not require separate manipulative parts like a separate holder and/or liner. A preferred embodiment of an absorbent article of the present invention is the unitary disposable absorbent article, diaper 20, shown in FIG. 1. As used herein, the term "diaper" refers to an absorbent article generally worn by infants and incontinent persons about the lower torso. The present invention is also applicable to other absorbent articles such as incontinence briefs, incontinence undergarments, absorbent inserts, diaper holders and liners, feminine hygiene garments, wipes, mops, bandages and the like.

Figure 1:
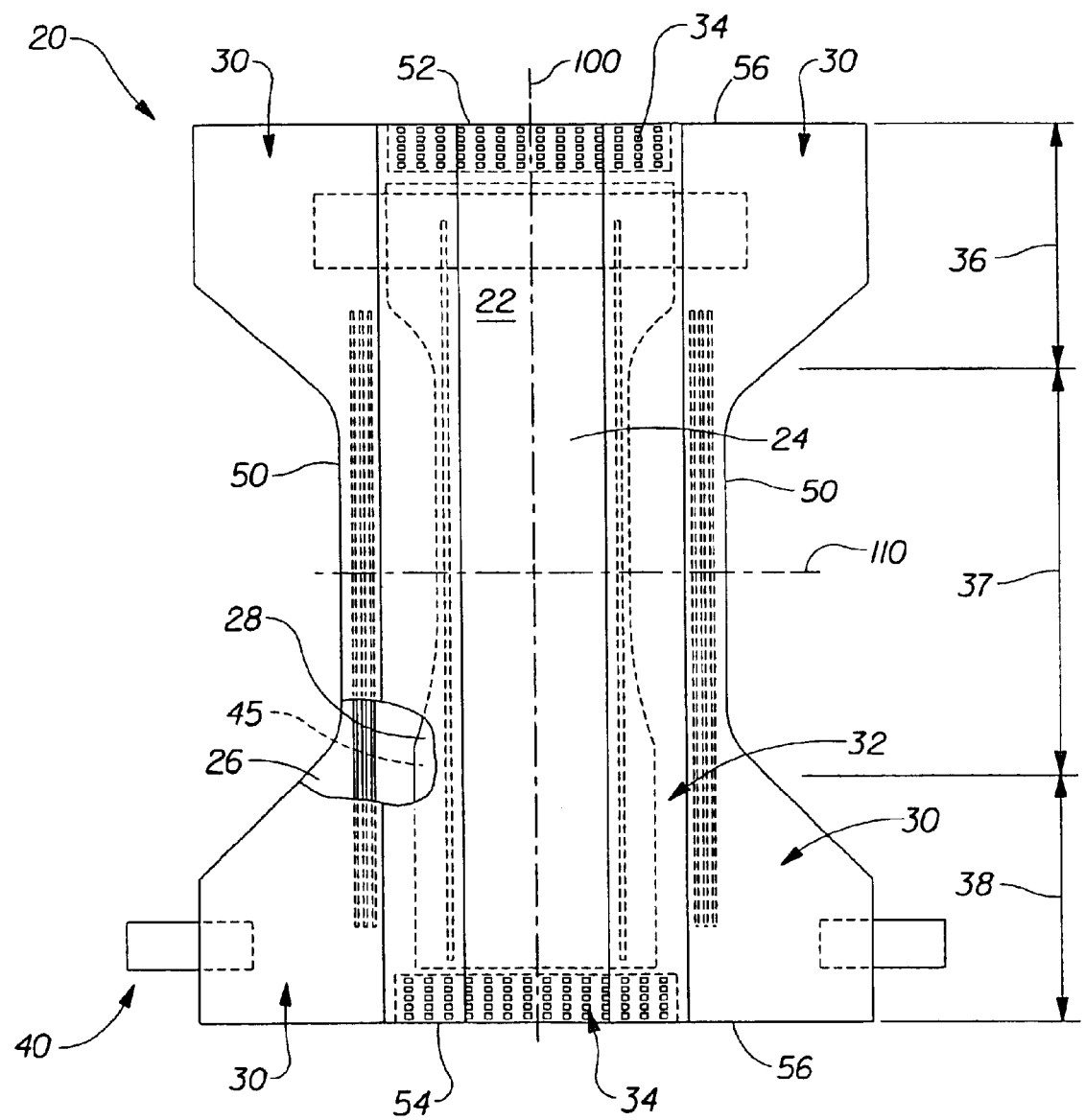
FIG. 1 is a plan view of a disposable diaper with portions cut away to reveal underlying structure.
Figure 2:
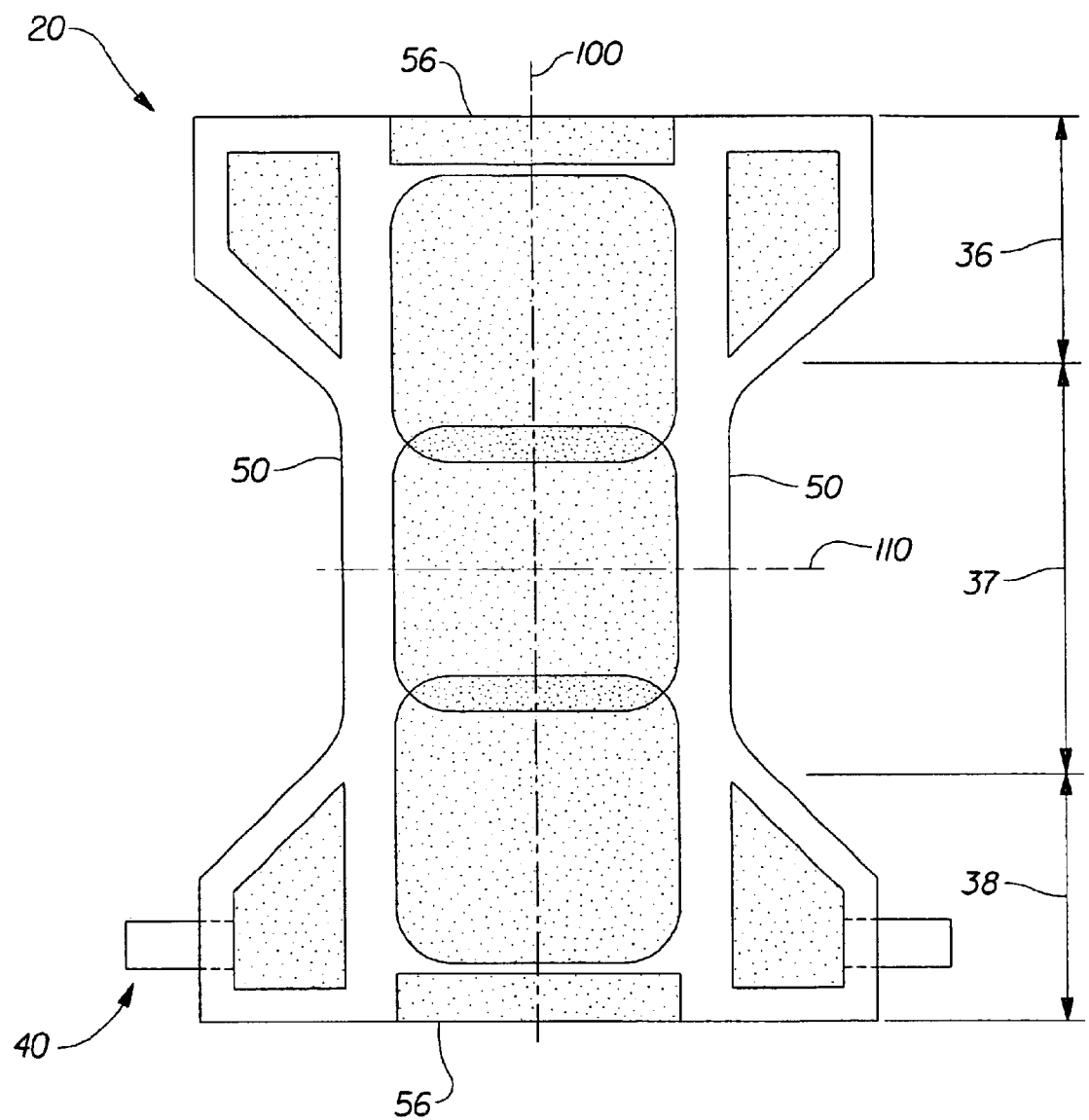
FIG. 2 is a plan view of a disposable diaper indicating potential placement locations of the present invention.

FIG. 1 is a plan view of the diaper 20 of the present invention in a flat-out, state with portions of the structure being cut-away to more clearly show the construction of the diaper 20. The portion of the diaper 20 which faces the wearer is oriented towards the viewer. As shown in FIG. 1, the diaper 20 preferably comprises a liquid pervious topsheet 24; a liquid impervious backsheet 26; an absorbent core 28 which is preferably positioned between at least a portion of the topsheet 24 and the backsheet 26; side panels 30; elasticized leg cuffs 32; an elastic waist feature 34; and a fastening system generally designated 40. The diaper 20 is shown in FIG. 1 to have a first waist region 36, a second waist region 38 opposed to the first waist region 36 and a crotch region 37 located between the first waist region 36 and the second waist region 38. The periphery of the diaper 20 is defined by the outer edges of the diaper 20 in which longitudinal edges 50 run generally parallel to the longitudinal centerline 100 of the diaper 20 and end edges 56 run between the longitudinal edges 50 generally parallel to the lateral centerline 110 of the diaper 20.

The containment assembly 22 of the diaper 20 preferably includes the topsheet 24, the backsheet 26, and the absorbent core 28 which is preferably positioned between at least a portion of the topsheet 24 and the backsheet 26. The containment assembly 22 constitutes the main structure of the diaper with other features added to form the composite diaper structure. The containment assembly 22 has an inner surface which generally is in contact with the body or in close proximity to the body when the article is worn. The containment assembly 22 also has an outer surface opposed to the inner surface which generally is in contact with or in close proximity to any garment that may be worn about the wearer's lower torso. The topsheet 24, the backsheet 26, and the absorbent core 28 may be assembled in a variety of configurations well known in the art. Exemplary containment assembly structures are described in U.S. Pat. No. 5,899,895 issued May 4, 1999 and U.S. Pat. No. 6,120,487 issued Sep. 19, 2000, which are hereby incorporated herein by reference.

The backsheet 26 is generally that portion of the diaper 20 which is disposed adjacent the garment-facing surface 45 of the absorbent core 28 and which prevents the excreta and/or exudates contained therein from soiling articles which may contact the diaper 20, such as bedsheets and undergarments. (The term "disposed" refers herein to the arrangement of an element in a particular physical relationship to other elements of the absorbent article.) Examples of suitable backsheet films include those manufactured by Tredegar Industries, Inc., or Terre Haute, Ind., USA, and sold under the trade names X15306, X10962, and X10964.

The backsheet 26, or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801 entitled "Web Materials Exhibiting Elastic-Like Behavior" issued to Chappell, et al. on May 21, 1996, and which is incorporated herein by reference. In alternate embodiments, the backsheet 26 may comprise elastomeric films, foams, strands, or combinations of these or other suitable materials with nonwovens or synthetic films.

In certain embodiments, the backsheet of the article may include zones which differ from each other in breathability and/or liquid permeability. For example, the backsheet may be higher in breathability and/or liquid permeability in zones which do not coincide with the absorbent core. The backsheet may be assembled of one or more layers and preferably includes at least one layer which is liquid impermeable, the liquid impermeable layer preferably located adjacent the absorbent core and preferably covers an area at least as large as the absorbent core.

In any case, at least a portion of the backsheet has low breathability, specifically has a water vapor transmission rate, WVTR, of less than about 2600 $g/m^2/day$. The portion of the backsheet with low WVTR may coincide with at least a portion of the absorbent core.

The topsheet 24 is preferably disposed adjacent the body-facing surface of the absorbent core 28 and may be joined to the absorbent core 28 and/or to the backsheet 26 by any attachment means known in the art. Preferably, at least a portion of the topsheet 24 is liquid pervious, permitting liquids to readily penetrate through its thickness. A suitable topsheet may be manufactured from a wide range of materials known in the art, such as porous foams, reticulated foams, apertured plastic films, or woven or nonwoven materials of natural fibers such as wood or cotton fibers, or synthetic fibers such as polyester or polypropylene fibers, or a combination of natural and synthetic fibers.

The absorbent core 28 may comprise any suitable absorbent material which is capable of absorbing and retaining liquids such as urine and other bodily exudates. The absorbent core 28 may include any of a wide variety of liquid-absorbent materials commonly used in disposable diapers and other absorbent articles, such as comminuted wood pulp, cellulose wadding, meltblown polymers, chemically stiffened, modified, or cross-linked cellulosic fibers, tissue, absorbent foams, superabsorbent polymers, absorbent gelling materials. Exemplary absorbent core structures are described in U.S. Pat. No. 4,610,678 issued Sep. 9, 1986 and U.S. Pat. No. 5,260,345 issued Nov. 9, 1993, both of which are hereby incorporated herein by reference.

The diaper 20 may include at least one waist feature 34 as shown, for example, in FIG. 1. The waist feature 34 preferably is disposed partially longitudinally outwardly from at least one of the waist edges 56 of the absorbent core 28 and generally forms at least a portion of the front end edge 52 and/or the back end edge 54 of the diaper 20. The waist feature 34 may comprise one or more separate elements affixed to the diaper 20 and/or may comprise an extension of another element of the diaper 20, such as the backsheet 26 and/or the topsheet 24. The waist feature 34 may be substantially inelastic or may be at least laterally elastically extensible to dynamically fit at the wearer's waist. The terms "elastic" and "elastically extensible" refer herein to the property of a material and/or an element of the diaper 20 whereby the material and/or the element can be elongated to a practical extent upon the application of tension and will substantially return to its original length or near its original length after the tension is released. Exemplary waist feature constructions include those described in U.S. Pat. No. 4,515,595 issued May 7, 1985 and U.S. Pat. No. 5,221,274 issued Jun. 22, 1993, both of which are hereby incorporated herein by reference.

The diaper 20 may also include a fastening system 40. The fastening system 40 preferably maintains the first waist region 36 and the second waist region 38 in a configuration so as to provide lateral tensions about the circumference of the diaper 20 to hold the diaper 20 on the wearer. The fastening system 40 preferably comprises a surface fastener such as tape tabs, hook and loop fastening components and/or hermaphroditic fastening components, although any other known fastening means are generally acceptable. Some exemplary surface fastening systems are disclosed in U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; the herein before referenced U.S. Pat. No. 5,151,092 issued to Buell on Sep. 9, 1992; and U.S. Pat. No. 5,221,274 issued to Buell on Jun. 22, 1993. In alternative embodiments, opposing sides of the article may be seemed or welded to form a pant. This allows the article to be used as a pull on type diaper, such as a training pant.

The diaper 20 may also include side panels 30 disposed in the back waist region 38, in the front waist region 36, or in both the front waist region 36 and the back waist region 38 as shown, for example, in FIG. 1 and other figures. The side panels 30 may be elastically extensible or nonextensible. An exemplar of an elastically extensible side panel is described in U.S. Pat. No. 5,669,897 issued Sep. 23, 1997, which is hereby incorporated herein by reference.

The diaper 20 may include at least one leg cuff 32 as shown, for example, in FIG. 1. Leg cuffs 32 are known in the art as leg cuffs, leg bands, side flaps, barrier cuffs, and/or elastic cuffs. The leg cuff 32 may be constructed in any suitable configuration known in the art, including those described in U.S. Pat. No. 4,695,278 issued Sep. 22, 1987, and U.S. Pat. No. 4,795,454 issued Jan. 3, 1989, which are hereby incorporated herein by reference.

In addition, the article of the present invention preferably comprises a thermal cell actuator. A "thermal cell actuator" as used herein refers to a thermal cell actuator which actuates the performance of a useful function on the article. Some examples of useful functions the thermal cell actuator may perform include altering the properties of at least a portion of the article or environmental conditions between the article and the wearer. In any case, the useful function is in some way related to or caused by a reduction or increase of the temperature of the thermal cell actuator or a portion of the article.

The thermal cell actuator can be activated by an action of the wearer or caregiver or by environmental conditions between the article and wearer. For example, actions of the wearer or caregiver that can activate the thermal cell actuator may include the introduction of a normal force to compress a portion of the garment body or a tensile force to extend a portion of the garment body. Environmental conditions which may activate the thermal cell actuator include changes in temperature, moisture between the topsheet of the article and the wearer, relative humidity, etc.

The thermal cell actuator may provide a cooling effect, a heating effect, both heating and cooling effects, or the thermal cell actuator may function as a heat sink. A thermal cell actuator providing solely a cooling effect is referred to herein as a cooling device. A thermal cell actuator providing solely a heating effect is referred to herein as a heat source. A thermal cell actuator which can provide either a heating or cooling effect depending on its operation is referred to herein as a 2-way thermal cell actuator.

If the thermal cell actuator itself generates the heating or cooling effect it is referred to as an "effect-generating thermal cell actuator". Certain embodiments of effect-generating thermal cell actuators are electrically powered, and thus can sustain the thermal effect as long as a source of power is provided. Others are capable of generating the thermal effect for a period of time, then revert to ambient temperature.

Alternatively, the thermal cell actuator may require a separate device to heat or cool it (i.e., it does not generate any heating or cooling effect itself), thus it is merely a "thermal energy storage device". Such thermal energy storage devices may be cooled or heated to a desired temperature and placed on or near a portion of an absorbent article to transfer heat out of a portion of the article (i.e., it behaves as a heat sink) to cool at least a portion of the article or transfers heat into a portion of the article to heat at least a portion of the article. Thermal energy storage devices are preferably capable of holding the desired temperature for as long as typically needed (i.e., the entire intended wearing period of the article), which may be as short as 30 seconds, but preferably is several minutes hours, and in certain preferred embodiments up to several hours.

In certain preferred embodiments, the heat flow is to or from the wearer and the thermal cell actuator 603 while heat flow with the environment outside the diaper may be controlled as shown in FIG. 5. If necessary to limit heat flow between the article and the outside environment, additional insulation can be added 604 or 606 between the thermal cell actuator 603 and the outside environment to further control heat transfer. Such insulation can be added either disposed between outer structure 605 and actuator 603 as at 604 or disposed on outer structure 605 as at 606 so as to be further outboard of inner structure 601. Suitable examples of heat insulation layers are typically porous materials with entrained air such as high loft nonwovens, open or closed cell foams, cellulose waddings, and the like.

The thermal cell actuator may be a single-use device which is intended to be thrown away once used or the thermal cell actuator may be reusable. Certain embodiments may act as "effect-generating thermal cell actuators" in their first use, and then may be reusable as a thermal energy storage device thereafter. Further, the thermal cell actuator may be integral to the article, may be separable from the article, or might not actually be connected to the product at all, but merely be held in place by the caregiver when needed. In such embodiments, the thermal cell actuator actuator is herein known as a "fully external thermal cell actuator" and is intended to be used with an article which comprises at least some element which is responsive to temperature increases or decreases.

In addition the thermal cell actuator may function as a heat sink to manage abrupt changes in heating an absorbent article. These abrupt changes in heat can be due to urination, defecation, or an increase in activity of the wearer. In one embodiment, a phase change materials may be incorporated into the thermal cell actuator.

Exemplary Heat Sources

Thermal cell actuators that generate heat are herein referred to as heat sources. The heat sources are intended to provide an extra source of heat beyond the heat provided by the wearer. The heat source may comprise any device or material which generates heat. For example, the heat source may generate a temperature change via any internal power source, such as battery or solar powered heaters, an exothermic chemical reaction, latent heat from phase changes, or a separable, potentially re-usable, heat pack. Further, the heat source may generate a temperature change using a thermoelectric effect such as the Peltier Effect or via resistive heating. Alternatively, the heat source may include a heat storage device which is heated to a high temperature by some external device and can maintain an elevated temperature for a period of time.

In embodiments employing heat sources producing heat from latent heat from phase changes, heat may be released during solidification of, for example, a super-cooled or super-saturated fluid solution. Since phase changes are reversible, this type of heat source may be re-usable (i.e., the heat source may be re-used on other absorbent articles). A suitable heat source utilizing the latent heat from a phase change is available as the Re-Heater Heat Pack marketed by Source Marketing International, INC. of Dallas, Tex. The patents below disclose not only certain chemicals which when mixed create exothermic solutions, as well as a method for packaging the chemicals prior to use. For example, exothermic solutions may be created by incorporating water and particular solutes (including but not limited to aluminum sulfate, aluminum chloride, aluminum bromide, ferric chloride, or potassium aluminum sulfate) into separate compartments within a sealed packet, the compartments being separated via a frangible or otherwise releasable seal. As an example embodiment, pressure upon the water compartment could break the frangible seal, allowing the water to mix with and dissolve the solute, creating an exothermic solution. Other systems which release heat are described in more detail in U.S. Pat. Nos. 4,462,224; 5,792,213; 5,545,197; 5,423,996; 5,552,075; and 5,650,090, all of which are incorporated herein by reference. Additional suitable heat sources based on latent heat release during phase changes are described in U.S. Pat. Nos. 5,805,766; 5,476,490; 5,662,096; 4,077,390; 5,897,580; 5,736,110; 5,275,156; 4,460,546; 4,899,772; 4,580,547; 5,056,589; 5,143,048; 708,549; 3,643,665; 3,951,127; and 4,451,383, all of which are incorporated herein by reference.

In embodiments wherein the heat source acts as a heat storage device, any suitable materials may be included in the heat storage device, but solid and liquid forms are preferred over gaseous forms because solids and liquids generally more effectively maintain the desired temperature when separated from the external heating system. If solid materials are used, relatively small particles are preferable to allow the packet to be flexible to conform to surfaces, such as that of the article or wearer and provide greatest contact with the area being heated. Preferably, the particles are less than about 10 mm in their largest dimension, more preferably less than about 5 mm, and even more preferably less than about 1 mm. The heat storage device may contain typical absorbent materials (including wood pulp fibers, cellulose fibers, superabsorbent polymers, sponges, foams, etc.) including at least a low level of water (e.g., preferably less than about 5% to about 10% by weight), or may include small particles of other suitable materials including but not limited to polypropylene, polyethylene, nylon, steel, polystyrene, rubber, and the like. Alternatively, the heat storage device may contain a gel or a liquid such as water, ethylene glycol, or any other suitable liquid or gel. Exemplary heat storage devices are described in U.S. Pat. Nos. 4,920,964; 4,891,501; and 5,417,276; all of which are incorporated herein by reference. Other suitable heat storage devices are available under the names "Hot n' Cold Pack" from Sunbeam-Oster Household Products of Schaumburg, Ill.

U.S. Pat. Nos. 4,741,338; 4,860,748; 5,197,294; 4,483,021; 4,470,263; and 5,800,490 describe thermoelectric heating devices which utilize the Peltier Effect and are suitable for heating at least a portion of the article or the environment between the wearer and the article. All of these patents are incorporated herein by reference. These devices typically need a power source. The power source for the Peltier heating device may be any suitable power source including household AC power, a battery, or solar power.

In yet other embodiments of the present invention, electric power may be used to generate heat by mechanisms other than the Peltier Effect, such as, but not limited to resistive heating. U.S. Pat. Nos. 5,486,680; 4,665,308; 5,772,185; 4,705,935; and 5,230,333 describe electric powered heating devices which are also suitable for heating at least a portion of an article or the environment between the wearer and the article.

The power source for the heat source may be household AC power, a battery, and solar, or any other known energy source suitable for use in the article of the present invention. Further, the heat source may include a singular heat generating mechanism or a combination of heat generating mechanisms, such as chemically based (chemical reaction or phase change based) and electrically powered heat generation. A suitable combination heat source system is disclosed in U.S. Pat. No. 5,805,776 which is incorporated herein by reference.

As described above, the heat source may comprise an exothermic chemical reaction. The exothermic chemical reaction may be an oxidation reaction driven by exposure of a suitable chemical system to air or other activating ingredient or ingredients. Suitable oxidative exothermic heat sources are described in U.S. Pat. Nos. 5,741,318, 5,918,590, and pending U.S. application Ser. No. 08/623,752 filed Mar. 29, 1996 which discloses addition of water to the heat cell to activate the exothermic chemical reaction. The exposure of the oxidative chemical system to its activating ingredient(s), typically air or water, may be accomplished by any known means including removal of an impermeable seal or cover or by physically breaking a seal or portion of the thermal cell actuator. The mechanism of exposing the oxidative chemical system to its activating ingredient(s) may also involve an additional step for the user (e.g., removal of a seal), or be a result of normal handling of the article during the process of applying it to a wearer.

Exemplary Cooling Devices

Thermal cell actuators that remove heat are herein referred to as cooling devices. Cooling devices are intended to provide cooling of the article or a portion thereof below the wearer's body temperature or to maintain a portion of the article at a specific target temperature. The cooling device may comprise any device or material which generates a cooling effect. For example, the cooling device may generate a temperature change or maintain a target temperature by means of thermodynamic effects of phase changes (such as via volatile liquids, which would reduce the temperature via evaporative cooling or phase change materials which undergo an endothermic phase transition at or between body and ambient temperatures), endothermic chemical reaction, the creation of a solution having a negative heat of solution, or the cooling device may generate a cooling effect using a thermoelectric effect such as the Peltier Effect. Cooling devices may also contain phase change materials that absorb heat while undergoing a phase transition in the direction of increasing temperature such as melting waxes. Alternatively, the cooling device may include a heat sink which is cooled to a low temperature by some external device and can maintain a relatively cool temperature for a period of time. When the heat sink cooling device is placed on or near the portion of the article to be cooled, the cooling device transfers heat from the article to itself, lowering the temperature of at least a portion of the article or the environment between the wearer and the article.

Exemplary phase change systems which result in cooling effects by utilizing water/urea phase change materials can be found in U.S. Pat. Nos. 5,552,075; 5,650,090; and 5,423,996 issued to Salyer on Sep. 3, 1996; Jul. 22, 1997; and Jun. 13, 1995 respectively, each of which is incorporated herein by reference. These patents disclose not only certain chemicals which when mixed create endothermic solutions, but means for packaging the chemicals prior to use. For example, endothermic solutions may be created by incorporating water and particular solutes (including but not limited to $Na_2HPO_4*12H_2O$, $Na_2SO_4*10H_2O$, $Na_2CO_3*10H_2O$, NH4NO3, KCl, NH4Cl, KNO3, NaNO3, KCNS, NH4CNS, Urea, NaCH3COO*3H2O) into separate compartments within a sealed packet, the compartments being separated via a frangible or otherwise releasable seal. Pressure upon the water compartment, for example, could break the frangible seal, allowing the water to mix with and dissolve the solute, creating an endothermic solution. Suitable products utilizing such technology can be purchased under the name "Instant Cold Pack" by Baxter Healthcare Products and Woodlets, Inc. of Buffalo, N.Y. Exemplary endothermic reaction systems are described in more detail in U.S. Pat. Nos. 4,462,224; 4,967,573; 5,792,213; 5,545,197; 5,431,022 and previously referenced U.S. Pat. Nos. 5,423,996; 5,552,075; and 5,650,090, all of which are incorporated herein by reference.

In embodiments wherein the cooling device includes a heat sink, any suitable materials may be included in the cooling device, but solid and liquid forms are preferred over gaseous forms as solids and liquids generally more effectively maintain the desired low temperature when separated from the external cooling system. Further, if solid materials are used, relatively small particles are preferable to allow the packet to be flexible to conform to surfaces, such as that of the article or wearer, and provide greatest contact with the area being cooled. As discussed with heat storage devices, preferably, the particles are less than about 10 mm in their largest dimension, more preferably less than about 5 mm, and most preferably less than about 1 mm. The heat sink device may contain typical absorbent materials (including wood pulp fibers, cellulose fibers, superabsorbent polymers, sponges, foams, etc.) containing at least a low level of water (e.g., preferably less than about 5 to about 10% by weight, or may contain small particles of other suitable materials including but not limited to polypropylene, polyethylene, nylon, steel, polystyrene, rubber, and the like. Alternatively, the heat sink device may contain a gel or a liquid such as water, ethylene glycol, or any other liquid or gel. Exemplary heat sink style cooling devices are described in previously referenced U.S. Pat. Nos. 4,920,964; 4,891,501; and 5,417,276. All of these patents are incorporated herein by reference. Other suitable heat sink products are available under the names "Hot n' Cold Pack" and "Cold Pack" from Sunbeam-Oster Household Products of Schaumburg, Ill. or "Cold Pack" by Chattanooga Corporation.

In embodiments wherein the cooling device includes a phase change material, the device stores the latent heat of a phase transition to act as a heat sink or buffer. These devices can possess a much higher heat per gram of material compared to systems based on simple heat capacity. These devices also may provide constant temperature control since the phase transition temperature can be precisely set by changing materials. Due to the reversibility of phase transitions, effects of a thermal cell actuator using phase transition materials may also be reversible. As a result, phase transition materials may function as a heat sink to manage abrupt changes in heat. The phase change temperature of the phase change material can be any suitable temperature. However, for diaper embodiments the phase change material preferably undergoes a phase change between 30 Celsius and 37 Celsius, more preferably between 32 Celsius and 35 Celsius. Various applications of phase change materials in articles are described in U.S. Pat. Nos. 5,722,482, 5,885,475, 5,366,801, 4,572,864, and 4,851,291.

Previously referenced U.S. Pat. Nos. 4,741,338; 4,860,748; 5,197,294; 4,483,021; 4,470,263; and 5,800,490 describe thermoelectric cooling devices which utilize the Peltier Effect and, in addition to being suitable for creating heating effects as previously disclosed herein, are suitable for cooling at least a portion of the article or the environment between the wearer and the article.

Exemplary 2-way Thermal Cell Actuators

Thermal cell actuators that can both generate and remove heat are herein referred to as two-way thermal cell actuators. Temperature regulation may be useful to improve wearer comfort and thermal cells which can both add and remove heat may function to regulate temperature within an article. As previously discussed, a thermal cell actuator which can provide either a heating or cooling effect within an article depending on its operation is referred to herein as a two-way thermal cell actuator. Certain two-way thermal cell actuators can be useful, for example, to prevent undue cooling or heating of the environment between the article and the wearer and provide a controlled environment.

Certain of the above described thermal cell actuators may act as two-way thermal cell actuators. For example, most heat storage devices can be heated to store high temperature or can be cooled to store low temperature. Further, Peltier cells can provide either heating or cooling effects based on direction of current through the cell, thus with appropriate circuitry a given Peltier cell be a two-way thermal cell actuator.

In other embodiments, a two-way thermal cell actuator can be constructed using a two-part system wherein a first part comprises any of the aforementioned heating devices and a second part comprises any of the aforementioned cooling devices. For example, a two-way thermal cell actuator may contain both an exothermic reaction-based heating cell in one part and an endothermic reaction-based cooling cell in another part. Alternatively, the two-way thermal cell actuator may contain both a phase change-based heating cell in one part and an endothermic-based cooling cell in another part. Any types of heating and cooling cells may be combined into a single thermal cell actuator such that the user can choose to use the heating effect at one point in time, and reuse the pack as a cooling pack at another time. Further, the two-way thermal cell actuator may comprise a plurality of individual heating and cooling packs to allow a plurality of uses. For example, the two-way thermal cell actuator may include two or more heat source devices and two or more cooling devices.

In any case, the thermal cell actuator or any portion thereof may be disposable or reusable. For example, in some embodiments the thermal cell actuator may be reused repeatedly utilizing the same mechanism for creating a heating effect in each re-use or alternatively a cooling effect in each re-use. In other embodiments the thermal cell actuator may include one mechanism to generate the heating or cooling effect on one use and another mechanism on subsequent uses. For example, a heating device may utilize an exothermic reaction to generate a heating effect on one use and then may be reused as a heat storage device. Further, a cooling device may utilize an endothermic reaction to generate a cooling effect on one use and then may be reused as a heat sink.

Figure 3:
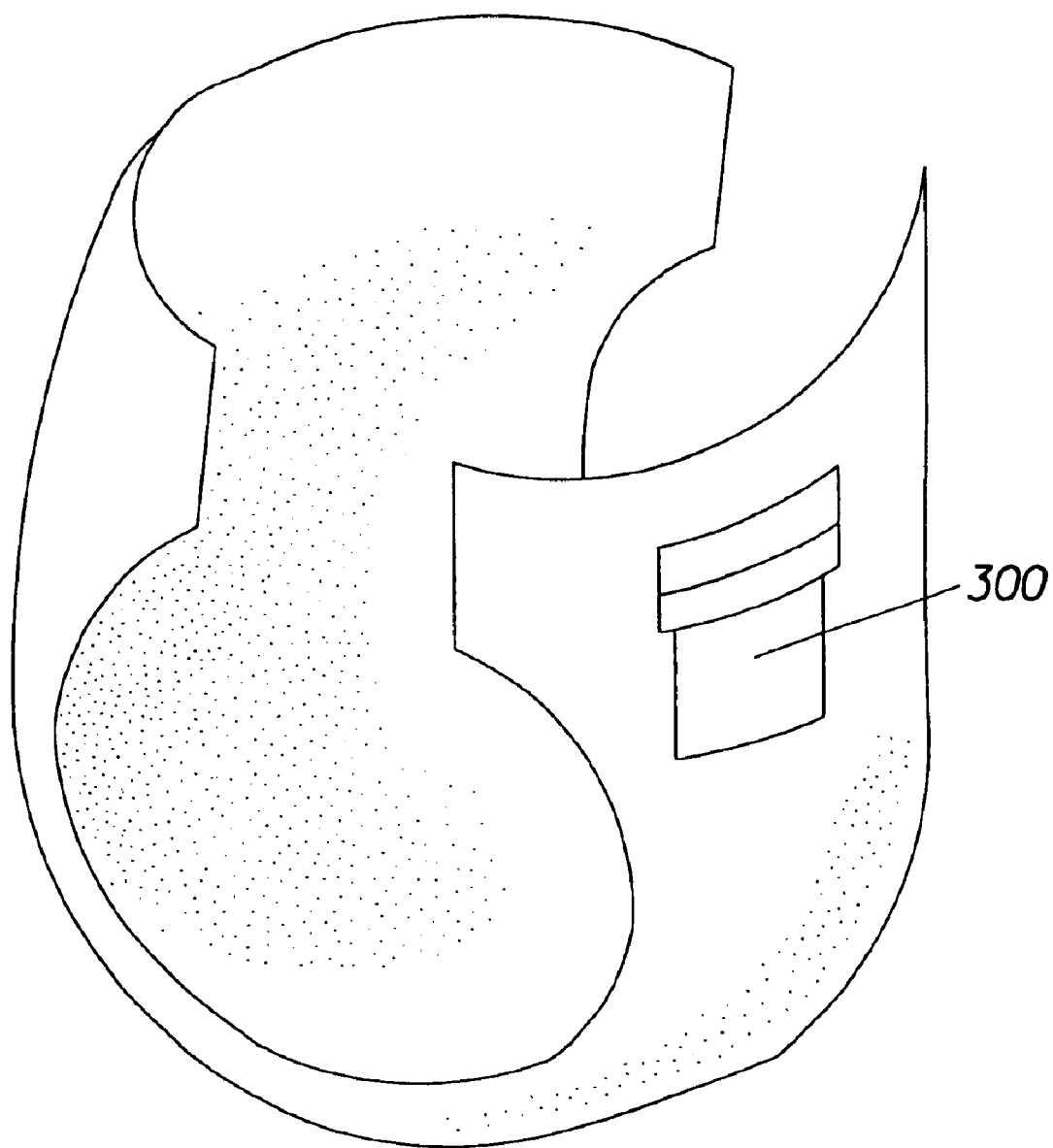
FIG. 3 is an isometric view of one embodiment of the present invention shown as it may appear when worn.

Further, the thermal cell actuator may be permanently joined to the article or removable therefrom. The thermal cell actuator may be joined or placed in contact with any portion of the article including but not limited to a location adjacent to the topsheet 24 or backsheet 24 or between the topsheet and backsheet. A removable thermal cell actuator may be constructed either by including frangible bonds to facilitate thermal cell actuator removal from the article or by attaching the thermal cell actuator to the article with separable fasteners, including pressure sensitive adhesive fasteners, mechanical fasteners, hook and loop fasteners, interlocking fasteners, or any other suitable fasteners. Alternatively, the article may include a pocket 300 or other structure into which the thermal cell actuator may be placed, one example of which is shown in FIG. 3. In such embodiments, it can be used as an Active External Change Aid Device, as disclosed in co-pending U.S. application Ser. No. 09/778,687, entitled Active Change Aids for External Articles, filed in the names of Kline, et al. on Feb. 7, 2001, which is incorporated herein by reference. Removable thermal cell actuators may be constructed in various forms, including small packets in which the user fills a bladder with hot (or cold) water or other fluid, solid, or gel material and attaches it to the article in the region to be heated or cooled.

Exemplary Triggering Mechanisms

The thermal cell actuator of the present invention may be triggered by non-urine based mechanisms within the article. Among the suitable triggering mechanisms are: 1) force-based mechanisms or 2) detection of a change in a measurable parameter from a sensor which activates the thermal cell actuator.

Force based triggering mechanisms may include, for example, application of a normal force or a tensile force to a structure. The application of the force may cause at least one layer of a structure 220 to rupture or become opened at aperture 222, thus exposing at least two reactants to each other 215 (and said reactants create an endothermic or exothermic effect as they react with each other) as seen in FIG. 4. A mechanical activator 502 in the form of an elongated strip, rod; or the like preferably extends from structure 220 to the inner surface of secondary topsheet 43 to a second retention point. As illustrated and described herein, activator 502 is formed from a substantially inextensible material, or from a material having an extensibility that is significantly lower than the extensibility either of secondary topsheet 43. Activator 502 is connected at one end 504 thereof with secondary topsheet 43 by a suitable second retention point, such as by adhesive layer 506, or by heat or ultrasonic sealing, friction or the like, so that end 504 of activator 502 is firmly and securely held by secondary topsheet 43. The opposite end 508 of activator 502 is connected with structure 220 by a releasable connection arrangement, such as by a pressure-sensitive adhesive layer 510, or the like. Additionally, end 508 of activator 502 has a sufficiently large area to define a cover portion that completely overlies and surrounds aperture 222 provided in structure 220. The application of tension to the garment results in relative movement between the first retention point of structure 220 and other diaper structure 44, defined by adhesive layer or spot 500, and the second retention point of activator 502 and secondary topsheet 43. The activation force may also be provided by a caregiver who peels a tab exposing an opening in the actuator. Example structures which trigger under normal loads are included in previously referenced U.S. Pat. No. 4,462,224; 5,792,213; 5,545,197; 5,423,996; 5,552,075; and 5,650,090, all of which are incorporated herein by reference. Example structures which trigger under tension loads are included in U.S. Pat. No. 5,520,274 and pending U.S. Application Ser. No. 09/481,042 entitled Disposable Garment Having an Expandable Component, filed in the name of Wise, et al. on Jan. 11, 2000. Alternatively, the force application may act to operate a switch which turns on or off an electrically-based thermal cell actuator—the switch could react to normal loads (as a typical pushbutton) or tensile loads (as a typical pull-chain on a light fixture). Properties measured by sensors may include temperature, humidity, concentration of a chemical (such as concentration of urine in the absorbent core or in vapor phase in the environment between the article and wearer), or pH.

Exemplary Tailorable Heat Amounts

It may be desirable to adjust the amount of heat to be added or removed from an article to optimize the effect of the thermal cell actuator to improve wearer comfort. The amount of heating and cooling effect may be varied by changing the amount of mass of reactants or materials present in the thermal cell actuator. Specific embodiments are envisioned in which the user or caregiver can determine how much effect to deliver and use more or less depending on the expected need during the wearing period of the article.

For example, the article may be provided with a pocket in which to place the thermal cell actuator or other location for attaching the thermal cell actuator to the article, as already discussed. The thermal cell actuators may be designed as packets, insertable into or attachable to the article. In such embodiments, the user may add only one packet if the need for cooling is expected to be low (i.e., a short expected weartime during a relatively inactive wearing period). Alternatively, the user could add more than one packet if the need for cooling is expected to be high (i.e., a long expected weartime or during a relatively active wearing period).

Exemplary Uses of Thermal Cell Actuators with Absorbent Articles

The thermal cell actuator of the present invention may actuate one or more of several types of changes within the article or environment between the article and the wearer. For example, the heat produced by the thermal cell actuator may cause a material to shrink within the article, thus effect a dimensional change of at least a portion of the article.

Exemplary heat shrinkable materials are found in the following U.S. Pat. Nos. 4,303,571; 4,543,154; 4,515,595; each of which is incorporated by reference here. Further, the heat produced by the thermal cell actuator may cause a phase change such as evaporation of a volatile liquid to result in a cooling effect internal to the product, melting of a solid into a liquid to allow the solid to become mobile within the product. Melting of a solid can be utilized to cause a material to flow from the article to the wearer, such as a lotion or other skin treatment or other material transferred from the article to the skin to at least partially coat the wearer's skin. Exemplary materials that flow might be altered are found in the PCT Publication: WO 99/45973. Alternately, a viscosity may be raised or lowered by removing or adding heat, respectively. Regulation of the heat may also increase or regulate the flow of materials. The thermal cell actuator may also provide the energy necessary to activate a chemical into a different state. For example, application of heat may activate an adhesive to become tacky and removal of heat may deactivate an adhesive to reduce adhesion values.

The cooling effects of a thermal cell actuator may be used to prevent a material from flowing out of the article at body temperature, thus maintaining the material internal to the article instead of transferring out of the article. Regulating of the cold temperature may also limit or regulate the flow of materials such as the migration of diaper lotions. The cooling effect may also be used to lower the temperature between the article and the wearer to improve wearer comfort, and may even lower internal relative humidity between the article and wearer. In a preferred embodiment, the thermal cell actuator is placed immediately below the material desired to flow. Alternatively, the material desired to flow is placed directly on the surface of the thermal cell.

In one embodiment for controlling environmental conditions between an article and the wearer includes a humidity sensor and a Peltier device. The sensor provides a signal to the Peltier device which triggers the Peltier device to provide either heating or cooling to control internal humidity. Similarly, a temperature sensor may be combined with a Peltier device to control temperature of the environment between the wearer and the article to a temperature closer to the surface temperature of skin not covered by the article. Suitable temperature sensors include thermistors and thermocouples. Preferably the device will cool to about 15 to 25 Celsius, more preferably 17 to 21 Celsius.

In another embodiment of the present invention, the diaper 20 includes a thermally activatable adhesive which acts to hold the article or some portion thereof in place during at least a portion of the article's use. For example, the longitudinal, lateral, and/or the z-directional placement (i.e., direction normal to the wearer) of the article may be maintained by the thermally activatable adhesive. Alternatively, the adhesive may be used to adhere a portion of the article to another portion of the article or a different article. The thermally activatable adhesive may also be used as a disposal means for holding the article in a proper configuration for disposal after use.

Suitable activatable, deactivatable, and thermally reversible adhesives are disclosed in co-pending U.S. patent application Ser. No. 09/504,765, Disposable Article with Deactivatable Adhesives, filed Feb. 15, 2000 and Ser. No. 09/504,485, Absorbent Article with Thermally Activatable Adhesives, filed Feb. 15, 2000. These patent applications are hereby incorporated by reference herein.

Exemplary Embodiment Including Water Vapor Condensation Inside the Article

One use of a thermal cell actuator is to regulate or control relative humidity within an article by promoting condensation of water vapor. Thermal cell actuators of the cooling device type are able to decrease the temperature in a specific region of the absorbent article thus, change the vapor pressure in that region. If the region is at a lower temperature than the skin of the wearer and the vapor can move to the region comprising the thermal cell actuator, this can lead to vapor condensation on the thermal cell actuator thus decreasing the relative humidity of the air adjacent to the skin. The condensation can therefore be used to remove excess heat from the wearer and allow for control of the relative humidity and microclimate (the climate conditions between the topsheet of the article and the wearer) even if low or no vapor is being exchanged with the outside environment. It is thus possible to use a diaper comprising a thermal cell actuators of the cooling device type to manage relative humidity, RH, in the article at low breathability thus avoiding problems of outside condensation on the backsheet as long the region having the lower temperature is thermally isolated form the backsheet. It is preferred to have an absorbent layer 602 or absorbent material close to the thermal cell actuator 603 to remove the condensate, such as shown in FIG. 5.

Exemplary Embodiment Including Changing Dimension and/or Modulus of a Structure

Temperature changes due to the action of a thermal cell actuator may be used to alter material properties within an article because polymers, which are typically used throughout disposable articles, decrease in modulus as temperature increases (and increase in modulus as temperature decreases). The thermal cell actuator can be positioned close to materials or portions of the product for which it is desirable to have different properties at application than during wearing. For example, it may be preferable to have a pull-on diaper with side panels that have a low load during application (to enable easy to pull on), yet have a high load during wearing to hold the product in place. In certain embodiments, the diaper can be configured such that, if the side panels are heated just prior to application, modulus decreases, as does application load. Thus, it is preferred for the thermal cell actuator to be adjacent the portion of the article intended to undergo a dimension or modulus change. Once the portion of the article cools to body temperature during wearing, modulus increases, as does wearing load.

In an embodiment of the present invention, the article may include a laminate. In such an embodiment in which properties change with temperature, a laminate composite can be built from laminating 2 or more materials together. If the laminate is assembled using thermally deactivatable adhesives, when exposed to cold, the adhesive looses its tack—effectively delaminating the structure. When a combination of deactivatable and non-deactivatable bonds (i.e., non-deactivatable adhesives or mechanical bonds of some type) are used in the laminate, a structure can be built that, when exposed to low temperatures, the deactivatable bonds break but the non-deactivatable bonds remain intact. This lowers the modulus of the structure. If one layer is strained relative to another during the assembly (especially if an elastomeric material is strained), the deactivatable bonds may prevent the elastomer from fully relaxing to zero strain until the deactivatable bonds are deactivated. Once deactivated, the elastomer may relax from its tensioned state and foreshorten the structure.

Exemplary Embodiment Including Breathability Change

Thermal cell actuators may be used to indirectly impact breathability of the article. For example, if the article includes materials made from certain shape memory polymers, such as DiAPLEX (Mitsubishi International Corp.), breathability of portions made from that material may be caused to increase or decrease by changing the local temperature above or below the activation point of the material. Activation temperature may be varied depending on the specific polymer formulation. Such materials are described in an article entitled, "Water Vapor Permeability of Shape Memory Polyurethane with Amorphous Reversible Phase" by Jeong, et. al in *Journal of Polymer Science: Part B Polymer Physics*, Volume 38, 3009–3017 (2000).

Exemplary Embodiment Including Odor Control by Cooling Heating, or Combination Thereof Thermal cell actuators providing a cooling effect, or a heating effect, or combination thereof can also be used to provide odor control for the bodily exudates such as feces, menses, urine and the like that are contained within the absorbent article during its use and/or disposal. Of specific interest to control are those malodorous vapors that arise from the exudates, particularly four-carbon to six-carbon compounds including: acids, alcohols, aldehydes, amines, esters, ketones, thiols, and the like, as well as the heterocyclic compounds such as indole and skatole.

Thermal cell actuators of the heat sink type such as phase change materials when undergoing a phase change from liquid to solid are able to decrease the temperature in a specific region of the absorbent article and thus change the vapor pressure in that region. If the region is at a lower temperature than the air surrounding the bodily exudates from whence the malodorous vapors arise and those vapors can move to the region comprising the thermal cell actuator. This can lead to vapor condensation on the thermal cell actuator thus decreasing the relative abundance of malodorous vapors that can offend the wearer, caregivers, or others in the vicinity of the wearer during the use and/or disposal of the absorbent article. In addition, the use of odor sorbents well known in the art, such as activated carbon, silica, zeolites and the like, when place in close proximity to a heat sink can be used in conjunction with such an embodiment to increase the capacity of such an odor control system by providing bulk storage for such malodorous vapors that condense.

Thermal cell actuators of the heating type when triggered by direct detection of malodorous vapors, or by their indirect detection such as by the presence of exudates in the absorbent article, or by user intervention using a mechanical or electrical device, or any other means can be used to release fragrance to mask the malodors. In one example, a heating type thermal cell actuator may initiate fragrance release by melting a waxy or gel protective coating of a fragrance impregnate, such as an activated carbon, silica, starch, zeolite, or other fragrance carrier known in the art. In another example, the heat source provides sufficient energy to overcome the binding affinity of a masking fragrance for its carrier, such as unprotected activated carbon.

A combination of cooling and heating type thermal cells as described above can be used to control malodors in absorbent articles such that the cooling provides condensation of malodorous vapors and the heating causes release of a masking fragrance for the malodorous vapors that do not condense.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. An absorbent article comprising:
   (1) a backsheet;
   (2) a liquid pervious topsheet joined to the backsheet;
   (3) an absorbent core disposed intermediate to the topsheet and the backsheet;
   (4) a thermal cell actuator which adds or removes heat from at least a portion of the absorbent article upon actuation so as to result in a useful function selected from the group consisting of:
      a) maintaining the article at a predefined temperature,
      b) maintaining relative humidity in a volume between a wearer and the article when the article is worn
      c) melting a material disposed on the article,
      d) changing a mechanical property of a different component of the article,
      e) changing the breathability of a component of the article, and
      f) changing the vapor pressure of a material disposed on the article; and
   (5) a triggering mechanism connected with the thermal cell actuator whereby a non-urine based-signal within the article causes the thermal cell actuator to add or remove heat from at least a portion of the absorbent article.

2. The absorbent article of claim 1 wherein the thermal cell actuator performs the function at a location between the backsheet of the article and the skin of the wearer in response to a change in relative humidity, moisture, or temperature.

3. The absorbent article of claim 1 wherein the thermal cell actuator performs the function in response to the application of a tensile force by a caregiver to extend a portion of the article, or in response to the application of a normal force to compress a portion of the article by a caregiver.

4. The absorbent article of claim 1 wherein the action of the caregiver is an application of a tensile force to peel a tab exposing an opening in the thermal cell actuator which allows for the activation of said actuator.

5. The absorbent article of claim 1 wherein the thermal cell actuator controls humidity or temperature in the article.

6. The absorbent article of claim 1 wherein the thermal cell actuator includes a Peltier cell.

7. The absorbent article of claim 1 comprising a thermal cell actuator that provides a constant temperature in a region of the article during use of the article of about 15° to about 25° Celsius.

8. The absorbent article of claim 7 wherein the thermal cell actuator is not in contact with the wearer's skin when the article is worn.

9. The absorbent article of claim 7 wherein the thermal cell actuator is in vapor communication with the wearer's skin such that vapor can condense inside the article.

10. The absorbent article of claim 7 wherein the thermal cell actuator is triggered by a user during application of the article.

11. The absorbent article of claim 7 wherein the constant temperature in the region is maintained for at least 1 hour.

12. The absorbent article of claim 1 wherein the thermal cell actuator changes a mechanical property of a different component of the article.

13. The absorbent article of claim 12 wherein the component of the article is a waist opening or a cuff opening.

14. The absorbent article of claim 1 wherein activation of the thermal cell actuator results in a change in the vapor pressure of a material disposed on the article.

15. The absorbent article of claim 14 wherein the thermal cell actuator provides at least a portion of the article with a temperature of less than about 25° Celsius.

* * * * *